United States Patent [19]

Carr et al.

[11] Patent Number: 4,604,214
[45] Date of Patent: Aug. 5, 1986

[54] REMOVAL OF NITROCRESOLS FROM DINITROTOLUENE WASTE STREAMS USING FENTONS REAGENT

[75] Inventors: Richard V. C. Carr, Allentown, Pa.; Carl J. Martin; Roland Gonzalez, both of Houston, Tex.; Thomas A. Albanese, Allentown, Pa.

[73] Assignee: Air Products and Chemicals, Inc., Allentown, Pa.

[21] Appl. No.: 766,849

[22] Filed: Aug. 16, 1985

[51] Int. Cl.$^4$ .............................................. C02F 1/72
[52] U.S. Cl. .................................. 210/759; 210/909; 568/934
[58] Field of Search ............... 210/759, 763, 903, 908, 210/909, 724; 568/934

[56] References Cited

U.S. PATENT DOCUMENTS

| | | | |
|---|---|---|---|
| 3,711,402 | 1/1973 | Zumbrunn et al. | 210/759 |
| 4,224,249 | 9/1980 | Kunz et al. | 260/580 |
| 4,230,567 | 10/1980 | Larbig | 210/737 X |
| 4,361,712 | 11/1982 | Herman et al. | 568/932 |
| 4,482,769 | 11/1984 | Toseland et al. | 568/934 |

FOREIGN PATENT DOCUMENTS 1031450 10/1964 United Kingdom .

OTHER PUBLICATIONS

Hugh R. Eisenhauer, Oxidation of Phenolic Wastes, Sep. 1964, pp. 1116-1128.
Edward J. Keating, Richard A. Brown and Edward S. Greenberg, Phenolic Problems Solved with Hydrogen Peroxide Oxidation, Dec. 1978.

*Primary Examiner*—Thomas Wyse
*Attorney, Agent, or Firm*—Russell L. Brewer; E. Eugene Innis; James C. Simmons

[57] ABSTRACT

This invention relates to a process for removing trinitrocresols and picric acid contaminants from a wastewater stream generated in the production of nitroaromatics, particularly dinitrotoluene, by the mixed acid technique. The process involves contacting the crude dinitrotoluene generated by the mixed acid technique with an alkaline medium to generate an alkaline wash water containing water soluble nitrocresols and picric acid therein. This wastewater then, is separated from the organic component or may be recycled for contact with further quantities of crude dinitrotoluene product from the reactor. When the concentration of the water soluble salts of trinitrocresols and picric acid is of sufficient concentration, the wash water is treated with aqueous acid in sufficient proportion to reduce the pH to a level from 3-4. After pH adjustment, the medium is contacted with hydrogen peroxide and a ferrous ion under conditions to effect oxidation of a substantial portion of the trinitrocresol to carboxylic acid, nitric acid and carbon dioxide.

10 Claims, No Drawings

4,604,214

REMOVAL OF NITROCRESOLS FROM DINITROTOLUENE WASTE STREAMS USING FENTONS REAGENT

TECHNICAL FIELD

This invention relates to an improved process for removing nitrocresols and organic water insoluble components from a nitroaromatic reaction product stream without generating an environmentally unacceptable aqueous discharge stream.

BACKGROUND OF THE INVENTION

Commercially, nitroaromatics, and particularly dinitrotoluene, are produced by the mixed acid nitration of toluene, the mixed acid being a mixture of concentrated sulfuric and concentrated nitric acid. In the production of dinitrotoluene process, for example, toluene is first nitrated to form mononitrotoluene and then separated from the spent acid aqueous phase. The crude mononitrotoluene is then dinitrated with fresh acid in a second nitration stage. As is known the dinitrotoluene product recovered from the dinitration reactor contains impurities, primarily nitrophenolics, such as nitrocresol and picric acid.

Traditionally, it has been common practice to remove the nitrophenolic materials from the organic dinitrotoluene phase because it has has been believed they adversely affect the performance of hydrogenation catalysts in the reduction of dinitrotoluene to form toluenediamine. Removal of nitrophenolic material from the dinitrotoluene reaction product has been achieved by contacting that product with alkaline materials to convert the nitrophenolic materials with the crude dinitrotoluene reaction product to water soluble salts. The water soluble salts then are discharged.

Recent environmental regulations have placed severe restrictions on the discharge of aqueous stress containing alkali metal salts of nitrophenolic materials. As is known these materials are not readily subject to biodegradation and then there is an unknown factor regarding the toxicity of the materials in the amounts that would normally be discharged to the environment. Therefore it is desired that techniques be developed to remove nitrophenolic materials from a dinitrotoluene reaction product without creating an environmentally unacceptable aqueous discharge stream.

U.S. Pat. No. 4,482,769, although not prior art to this application, discloses a process for separating trinitroorthocresol from a reaction product while leaving dinitroorthocresol in the dinitrotoluene product. The process involves selectively precipitating the dinitroorthocresol from an aqueous stream by contacting with alkaline material.

Patents which show the removal of nitrophenolic material from crude dinitrotoluene streams by the addition of alkaline material are British Pat. No. 1,031,450; and U.S. Pat. Nos. 4,224,249; 4,361,712 and 4,230,567. Only the '567 patent addresses the problem of disposal of the wastewater streams containing alkali metal salts of nitrophenolic material. As acknowledged in that patent, direct incineration of the wastewater stream is considered to be energy intensive and is unacceptable for that reason. The approach taken in the '567 patent involves a degradation process as opposed to a combustion process.

Phenolic materials have presented problems when present in minimal waste streams and have been removed by various treatments. The use of Fenton's reagent was suggested as a means for oxidizing phenol and substituted phenols to hydroquinone and muconic acid. Phenols containing metal directing groups such as chloro, carboxyl and nitro groups have also been oxidized through the use of Fenton's reagent. Eisenhower, *Oxidation of Phenolic Wastes*, 36 J. Water Pollution Control Federation, 1116 (1964).

SUMMARY OF THE INVENTION

This invention relates an improvement in a process for removing nitrocresol material produced in the nitration of aromatic compounds by the mixed acid technique. The improvement resides in contacting the resultant crude nitroaromatic product with an alkaline material to convert trinitrophenolic material therein to a water soluble salt, and thereby form a purified nitroaromatic organic/water-insoluble product and an aqueous by-product phase containing the alkali metal salt of trinitrophenolic materials; separating the aqueous phase from the organic phase; contacting the aqueous phase containing water soluble trinitrocresolic material with an acid, said acid being added in sufficient proportion to reduce the pH of the stream to below about 4 in said aqueous phase; contacting the aqueous phase with hydrogen peroxide and ferrous ion in sufficient proportion and under conditions to oxidize said trinitrocresolic material to nitric acid, carbon dioxide and carboxylic acid.

Advantages of the process include:

an ability to remove trinitrocresol contaminants by-products generated in nitroaromatic production without creating an environmentally unacceptable waste stream;

an ability to remove contaminants in a nonenergy intensive manner;

an ability to render such composition innocuous; and an ability to achieve optimum oxidation rates through the use of a continuous process.

DETAILED DESCRIPTION OF THE INVENTION

In the commercial manufacture of nitroaromatics, particularly dinitrotoluene, an aromatic compound is nitrated under liquid phase conditions using a mixture of concentrated nitric acid and sulfuric acid. In the production of nitroaromatics and particularly dinitrated products, e.g., dinitrobenzene or dinitrotoluene, some by-product nitrophenolic material is produced. This nitrophenolic material usually is in the form of nitrocresols, either dinitro or trinitrocresol, and picric acid. It is this by-product which must be removed from the crude reaction product from the nitration reactors without creating an environmentally unacceptable stream. Removal of this material is necessary from the nitroaromatic product as many believe the presence of nitrophenolic materials interferes with the catalyst in subsequent reduction of the nitro group.

In nitration processes the reaction product is removed from the nitration zone and passed to a separator where the organic phase is separated from the aqueous phase. According to the process herein, the crude nitroaromatic composition is contacted with a dilute aqueous alkaline-containing solution to convert nitrocresols and picric acid to water soluble salts thereby generating an organic phase and an aqueous phase. Conventionally aqueous alkaline material suited for converting the nitrophenolic material to water soluble salts include sodium carbonate, ammonium hydroxide, sodium hydroxide, sodium bicarbonate, potassium hydroxide, and other alkaline materials. Solution concentrations for achieving conversion to water soluble salts generally are from about 0.1 to 50% by weight, and generally from about 1 to 10% by weight.

Contacting of the crude organic product with an aqueous alkaline solution is at a temperature from about 25° to 80° C. typically at atmospheric pressure to about 50 psig. Normally contacting is done at or about 70° C. and atmospheric pressure as this appears to be the most convenient way of converting the nitrophenolic materials to water soluble salts. Neither temperature nor pressure is critical to the conversion step.

Once the crude nitroaromatic composition has been treated with aqueous alkaline material, an organic layer and aqueous layer are formed. The aqueous layer is separated from the organic layer by decanting leaving a top aqueous layer containing water soluble salts of nitrophenolic material e.g., water soluble salts of dinitrocresol and trinitrocresol. To maximize the effectiveness of the alkaline treatment, the aqueous alkaline mixture, after separation from the treated organic phase, is often recycled for contact with additional quantities of crude nitroaromatic product to enhance or increase the concentration of the water soluble salts in the aqueous phase and decrease the amount of unreacted aqueous alkaline material in that phase. Generally, the aqueous alkaline phase obtained on separation from the organic layer after nitration is recycled until the concentration of alkali metal salts of nitrophenolic material ranges from about 0.5 to 1.5% by weight usually 0.9-1.2% by weight.

When the concentration of water soluble nitrophenolic salt in the aqueous medium reaches from desired concentration, at least a portion of the aqueous phase is separated for further treatment and disposal of the water-soluble salts of nitrophenolic material. In contrast to the prior art, the aqueous phase containing water-soluble nitrophenolic salt is first treated with an acidic material under conditions sufficient to reduce the pH of the aqueous phase to below about 4.5 for contact with an oxidizing agent, preferably about 2-4. This reduction can be accomplished by the addition of an inorganic acid such as nitric acid or sulfuric acid. Since both of these acids are available as spent acids from the nitration process, nitric acid and sulfuric acid are preferred. Addition of the acid is done at temperatures from about 25°-80° C. and atmospheric pressure to about 50 psig, typically 25°-30° C. and atmospheric pressure. Although some oxidation of phenolic materials can be effected at a pH as high as 5, trinitrocresols do not oxidize under such conditions. Continuous oxidation is preferred since a constant pH may be maintained leading to optimum oxidation rates and optimum usage of peroxide. This occurs at a pH of about 3. A batch oxidation is less preferred because of the generation of a pH profile leading to slower rates of oxidation.

To effect oxidation of the trinitrocresol, a reagent referred to as Fenton's reagent comprising hydrogen peroxide and a ferrous iron source is added to the wastewater. At elevated temperatures, e.g. from 70° to 90° C., the trinitrocresols and picric acid are oxidized to nitric acid, carbon dioxide, and carboxylic acids within a reaction time of about one-half to one hour. Often these may be ring ruptured compounds which as soluble in acidic streams present as waste acid in a nitroaromatic plant. Complete mineralization of trinitrocresol to carbon dioxide and nitric acid requires 17 moles of hydrogen peroxide per mole of trinitrocresol. Sometimes not all of the trinitrocresol need be oxidized in order to provide for a stream combinable with other waste to produce an environmentally acceptable stream, therefore, lesser quantities of hydrogen peroxide may be used. Typically, for purposes of this invention from about 7 to 12 moles hydrogen peroxide are added per mole of trinitrocresol. As stated, sufficient hydrogen peroxide is added to the system to reduce the trinitrocresol content to about 150 to 600 or approximately 5 to 20% of that originally in the stream. This level is sufficiently low that the trinitrocresol or phenolic material when added to plant effluent does not precipitate on addition to an acidic waste stream. A weight ratio of peroxide to total nitrocresol material used is from 1.1 to 3.0 or preferably 1.3 to 1.8. In other words, the oxidation of the trinitrocresols to a level well below their solubility in the wastewater at temperatures of 30° C., and preferably as low as 20° C. In other words, if the wastewater stream were cooled to a temperature of about 20° C., no precipitation of trinitrocresol would occur and thereby create a hazard in wastewater disposal. This level is typically from 5-20% of the level in the original waste.

The ferrous ion used to catalyze the oxidation of nitrophenolic material is provided by a ferrous salt, typically ferrous sulphate. This is added in an amount to provide from $2.5-5 \times 10^{-}$M, and preferably $3-4 \times 10^{-3}$ molar concentration.

The following examples are provided to illustrate various embodiments of the invention and are not intended to restrict the scope thereof.

EXAMPLE 1

Into a 304 ml glass stirred tank reactor is charged 250 ml of dinitrotoluene alkaline wash water obtained on treatment of the reaction product from a dinitrotoluene plant. The vessel contents are agitated by means of two stainless steel impellers and the vessel raised to 70° C. by intermittent cooling coils. Three feed pumps are then activated with the composition of each of the feeds to the vessel and rates as follows.

Alkaline wash water containing water soluble salts of trinitrocresol $3.24 \times 10^{-3}$ moles ferrous sulfate heptahydrate per liter wash water—6.7 g/min Sulfuric acid wash water 6% $H_2SO_4$ and 6% $NHO_3$—0.14 g/min (as controlled by pH controller—set pH=3)

Aqueous hydrogen peroxide—8.06% by weight at 0.25 g/min., the weight ratio $H_2O_2$/trinitrocresol equaled 1.11:1 grams hydrogen peroxide per gram of trinitrocresol.

The reactor was permitted to achieve steady state (3.6 hours) at a pH=3±0.03 and samples were then removed for analysis for dinitroluene by gas chromotography and for dinitrocresols and trinitrocresols by high performance liquid chromotography (HPLC). The results of these analyses are shown in Table 1.

The wastewater treated with Fenton's agent was acidified to a pH=1 with concentrated sulfuric acid and no precipitate was observed. This shows sufficient oxidation of the trinitrocresol had taken place to produce an environmentally acceptable stream which would not precipitate on contact with waste acid water.

TABLE 1

Removal of Organics in Dinitrotoluene Alkaline Wash Water with Fenton's Reagent

|  | Alkaline Wash Water | Reactor Effluent | % Removal |
|---|---|---|---|
| Dinitrotoluenes | 1210 ppm | 802 ppm | 34 |
| Dinitrocresols | 136 ppm | 43 ppm | 68 |
| Trinitrocresols | 2602 ppm | 274 ppm | 89 |

EXAMPLE 2

The procedure of Example 1 was repeated in a 218 ml CSTR reactor with the feed rates set as follows.

Alkaline wash water—4.20 g/min containing $3.54 \times 10^{-3}$ moles ferrous sulfate heptahydrate/liter of waste water.

Acid wash water—0.090 g/min (as controlled by pH controller set at pH=3.30).

Aqueous hydrogen peroxide—0.25 g/min at 9.18% by weight.

The steady state reactor effluent was sampled and analyzed as in Example 1. The results are displayed in Table 2.

TABLE 2

Removal of Organics in Dinitrotoluene Alkaline Wash Water with Fenton's Reagent

|  | Alkaline Wash Water | Reactor Effluent | % Removal |
|---|---|---|---|
| Dinitrotoluenes | 1420 ppm | 742 ppm | 48 |
| Dinitrocresols | 254 ppm | 19 ppm | 93 |
| Trinitrocresols | 3818 ppm | 156 ppm | 96 |

What is claimed:

1. In a process for removing trinitrocresol material produced in the nitration of aromatic compounds by the mixed acid technique to produce a nitroaromatic compound, the improvement which resides in
   (a) contacting the resultant crude nitroaromatic product with an alkaline material to convert trinitrocresol material therein to a water soluble salt, and thereby form a purified nitroaromatic organic product and an aqueous by-product phase containing the alkali metal salt of trinitrophenolic material,
   (b) separating the aqueous phase from the organic phase,
   (c) contacting the aqueous phase containing water soluble trinitrocresol material with an acid, said acid being added in sufficient proportion to reduce the pH to a range from about 2-4.5;
   (d) contacting the aqueous phase at reduced pH with hydrogen peroxide and a ferrous ion under conditions to effect oxidation of the trinitrocresol material to carbon dioxide, nitric acid and carboxylic acid; and
   (e) disposing of said aqueous phase containing resultant oxidized trinitrocresolic material.

2. The process of claim 1 wherein the alkali metal used for contacting the nitroaromatic is an aqueous solution of alkali metal carbonate; alkali metal bicarbonate; or alkali metal hydroxide.

3. The process of claim 1 wherein said nitroaromatic produced is dinitrotoluene.

4. The process of claim 3 wherein the hydrogen peroxide is added in sufficient proportion to reduce the concentration of water soluble nitrophenolic material in the aqueous solution to about 5-20% by weight of that originally in the stream.

5. The process of claim 4 wherein the acid used to reduce the pH of the aqueous phase is sulfuric acid or nitric acid.

6. The process of claim 5 wherein the alkali metal bicarbonate, alkali metal carbonate, or alkali metal hydroxide present in the aqueous solution is from about 1 to 10% by weight.

7. The process of claim 6 wherein said alkali metal in said carbonate, bicarbonate and hydroxide is sodium.

8. The process of claim 4 wherein said ferrous ion is supplied by ferrous sulfate.

9. The process of claim 4 wherein the weight ratio of hydrogen peroxide to nitrocresol is from 1.1 to 3 parts per 1 part of trinitrocresol.

10. The process of claim 9 wherein the ferrous sulfate provided for furnishing ferrous ion in the reaction is maintained from 2.5 to about $5 \times 10^{-3}$ molar.

* * * * *